United States Patent [19]

Dubrowski

[11] 4,187,838
[45] Feb. 12, 1980

[54] EAR CLIP FOR FLATTENING OF PROTRUDING EARS

[76] Inventor: John Dubrowski, 515 Lakeshore Rd. West, Oakville, Ontario, Canada

[21] Appl. No.: 824,539

[22] Filed: Aug. 15, 1977

[51] Int. Cl.² .......... A61F 11/00; A61F 5/01
[52] U.S. Cl. .................. 128/76 R; D11/42; 63/14 R; 63/14 G; 132/9; 132/48 R
[58] Field of Search ........ 128/76 R, 2 Z, 151, 128/152, 410, 76 B; 63/14 R, 14 A, 14 G; D11/42; 179/107 H, 107 E, 182 R, 156 R, 157; 181/129, 130, 131, 132, 133, 134, 135, 137; 132/46 R, 52, 48 R; 24/81 CC, 73 AP

[56] References Cited

U.S. PATENT DOCUMENTS

| | | | |
|---|---|---|---|
| 2,040,083 | 5/1936 | Elliott et al. | 63/14 A |
| 2,151,706 | 3/1939 | Lieber | 179/156 R |
| 2,511,170 | 6/1950 | McCann | 63/14 A |
| 2,757,665 | 8/1956 | Tanikawa | 128/76 R |
| 3,958,430 | 5/1976 | Barron | 63/14 A |

FOREIGN PATENT DOCUMENTS

| | | | |
|---|---|---|---|
| 727602 | 6/1932 | France | 128/76 |
| 139895 | 4/1953 | Sweden | 128/152 |
| 208142 | 4/1940 | Switzerland | 128/76 |

*Primary Examiner*—Robert W. Michell
*Assistant Examiner*—Arthur S. Rose

[57] ABSTRACT

The specification describes an individual ear clip which fits on the ear auricle and which is secured to the hair of the user for the flattening of a protruding ear auricle. The ear clip comprises a resilient clip portion for clipping over the auricle helix and a body portion including a first relatively flat section for fitting against the inner surface of the helix, a second relatively flat section for fitting in the auricle concha and a narrow bent section joining the first and second sections and fitting over the auricle antihelix. The ear clip is provided with hair securing means for securing the ear clip to the user's hair and tautly holding same, thereby flattening the protruding ear auricle.

5 Claims, 3 Drawing Figures

EAR CLIP FOR FLATTENING OF PROTRUDING EARS

FIELD OF THE INVENTION

This invention relates to an individual ear clip for use in flattening protruding ears.

BACKGROUND OF THE INVENTION

Many people are faced with the problem of having noticeably protruding ears which detract from the person's appearance. In some cases, only one ear may protrude and in other cases, both ears may protrude. At the present time, the only reliable method of flattening the ear to the head is to perform surgery. This method has its obvious unappealing drawbacks.

To the knowledge of the present inventor, no one has yet developed an individual ear clip for the flattening of protruding ears, which is reliable, comfortable and essentially unnoticeable. The prior art attempts have produced ear clips which are awkward to use and extremely bulky so that they are easily noticed.

The present invention provides an individual ear clip which fits on the ear auricle and which is secured to the hair of the user for the flattening of a protruding ear auricle. The ear clip comprises a resilient clip portion which clips over the auricle helix and a body portion including a first relatively flat section for fitting against the inner surface of the helix, a second relatively flat section for fitting in the auricle concha, and a narrow bent section joining the first and second sections and for fitting over the auricle antihelix. The ear clip is provided with hair securing means for tautly securing the ear clip to the user's hair, thereby flattening the protruding ear auricle.

BRIEF DESCRIPTION OF THE DRAWINGS

The above as well as other features and advantages of the present invention, will become apparent from the following detailed description of the preferred embodiments, wherein.

DETAILED DESCRIPTION OF THE PREFERRED EMBODIMENTS

Figure 1:
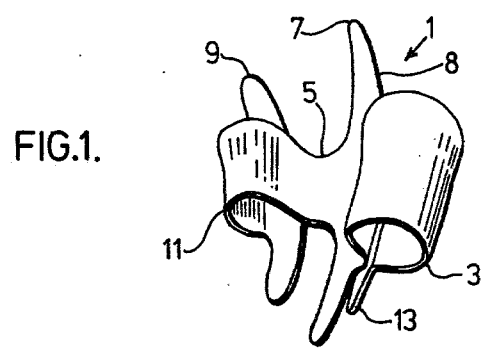
FIG. 1 is a perspective view looking down on a preferred structure of the ear clip according to this invention.

Referring to FIG. 1, the ear clip generally indicated at 1 includes a clip portion 3 and a body portion 5. The body portion includes a first and second essentially flat sections 7 and 9 respectively. These sections are preferably elongated with respect to the remainder of the ear clip as shown in FIG. 1. Joining the first and second flat sections is a bent or curved section 11. Ear clip 1 is provided with hair securing means which according to this embodiment, is in the form of an additional section 13 extending from clip portion 3.

Figure 2:
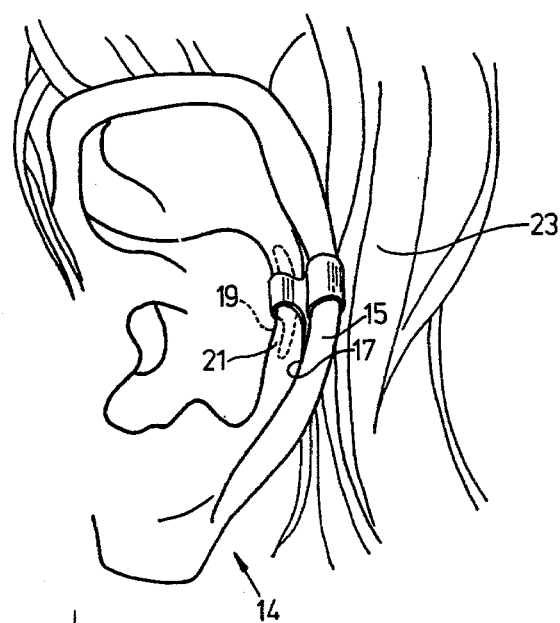
FIG. 2 is a side view of an ear auricle with the clip of FIG. 1 secured in position.

FIG. 2 shows a protruding ear auricle generally indicated at 14. The ear auricle comprises a helix 15 having an inner surface 17 an antihelix 21 and a concha 19.

When ear clip 1 is fitted on ear auricle 14, clip portion 3 is clipped over helix 15 with first section 7 abutting the inner surface 17 of the helix. Second section 9 is located in the auricle concha and bent section 11 fits over the auricle antihelix. As will be seen in FIG. 3, additional hair securing section 13 firmly abuts the back of the ear auricle.

The ear clip is made from resilient durable material such as a spring steel core covered with a plastic coating. Due to the resiliency of the clip, it accommodates various ear shapes and sizes. The clip portion is simply spread open and clamped over the auricle helix. The entire ear clip is preferably provided with a soft rubber lining thereby making it comfortable to the user and ensuring a firm fit to the ear auricle.

First section 7 preferably has an elongated arcuate shape, such that the rear wall 8 of section 7 curves and conforms with the inner surface 17 of the helix. Second section 9 may have the identical configuration to first section 7 for ease of manufacture of the ear clip.

Figure 3:
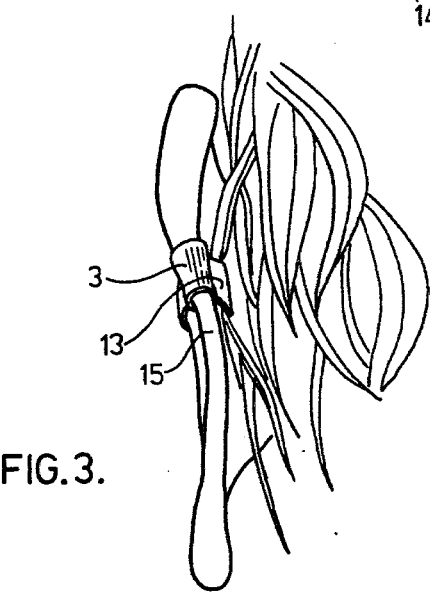
FIG. 3 is a rear view of the ear auricle shown in FIG. 2.

A person desiring to flatten a protruding ear first places the ear clip on the auricle as shown in FIGS. 2 and 3. When the clip is in place, second section 13 is lifted slightly from the back of the ear and strands of hair 23 are fitted between section 13 and the back of the ear auricle. The strands of hair are then pulled until they are taut, thereby flattening the ear auricle to the side of the head. The degree of tautness of the hair determines the amount of flattening. The rubber lining on section 13 will of course assist in holding the hair between the section and the back of the ear auricle.

With the present invention, should a person have only one ear auricle which protrudes with respect to the other auricle, it is possible to flatten the protruding auricle such that both auricles have the same appearance. In cases where both auricles protrude, two clips are used and both auricles are flattened to the desired position.

The size and shape of the clip, are such that it is virtually unnoticeable, especially when the user drapes a few strands of hair over the portion of the ear fitted with the ear clip. Although the size of the clip can obviously be varied, the preferred dimensions are as follows: the clip portion has a height of approximately ¼ inches; the first and second sections have a length of approximately ¾ inches; and the bent section joining the elongated flat sections has a height of approximately 3/32 inches.

There are of course other methods in which the ear clip could be clipped to the hair of the user. For example the hair could be clipped directly in the clip portion, or the clip could be provided with additional clamping or threading means for tautly holding the hair of the user and flattening the ear auricle to the side of the head.

Although various preferred embodiments of the invention have been described herein in detail, it will be apparent to one skilled in the art that variations may be made thereto without departing from the spirit of the invention or the scope of the apended claims.

The embodiments of the invention in which an exclusive property or privilege is claimed are defined as follows:

1. An ear clip for flattening of a protruding human ear, said ear clip being adapted to fit on an ear auricle of a human ear and comprising a resilient clip portion sized such that it may be clipped around the auricle helix of an ear auricle, a first elongated section having two ends, said first section being sized to fit against the inner surface of the auricle helix of an ear auricle, a second section sized to fit in the auricle concha of an ear auricle, said resilient clip portion being connected to said first section, between said ends such that first section will be positioned against the inner surface of the auricle helix of an ear auricle when said clip portion is clipped around the auricle helix of an ear auricle, a narrow bent section sized to fit over the auricle antihelix of an ear auricle, said bent section joining said first and second sections such that said second section will be positioned in the auricle concha of an ear auricle when said clip portion is clipped around the auricle helix of an ear auricle and said resilient clip portion being provided with hair securing means for flattening a protruding ear.

2. An ear clip as claimed in claim 1 wherein said first and second sections are elongated relative to said narrow bent section and said first section is arcuate along its length to conform to the shape of the inner surface of an ear helix.

3. An ear clip as claimed in claim 2 wherein said clip portion and said body portion are both provided with a soft rubber lining.

4. An ear clip as claimed in claim 3 wherein said hair securing means comprises an additional section extending from said clip portion and being provided with a soft rubber lining, the arrangement being such that when said clip portion is clipped over the auricle helix of an ear auricle said additional section firmly abuts the back of an auricle for clipping hair tightly thereunder for flattening a protruding ear auricle.

5. An ear clip as claimed in claim 4 wherein said ear clip has a spring steel core covered by a resilient plastic material.

* * * * *